(12) United States Patent
Han et al.

(10) Patent No.: US 11,751,796 B2
(45) Date of Patent: *Sep. 12, 2023

(54) SYSTEMS AND METHODS FOR NEURO-FEEDBACK TRAINING USING VIDEO GAMES

(71) Applicant: BrainCo Inc., Somerville, MA (US)

(72) Inventors: Bicheng Han, Somerville, MA (US); Tianhe Wang, Revere, MA (US); Max Newlon, Allston, MA (US); Joanne Wylie, Allston, MA (US); Chengbang Zhou, Zhangqiu (CN); Jianlin Zhou, Everett, MA (US); Xiang Yu, Brighton, MA (US); Bowei Huang, Liuzhou (CN); Zhaoyi Yang, Boston, MA (US)

(73) Assignee: BRAINCO, INC., Somerville, MA (US)

( * ) Notice: Subject to any disclaimer, the term of this patent is extended or adjusted under 35 U.S.C. 154(b) by 362 days.

This patent is subject to a terminal disclaimer.

(21) Appl. No.: 15/398,691

(22) Filed: Jan. 4, 2017

(65) Prior Publication Data

US 2018/0184936 A1    Jul. 5, 2018

(51) Int. Cl.
| | |
|---|---|
| *A61B 5/375* | (2021.01) |
| *A61B 5/00* | (2006.01) |
| *A63F 13/46* | (2014.01) |
| *A63F 13/28* | (2014.01) |
| *A63F 13/25* | (2014.01) |
| *A63F 13/355* | (2014.01) |
| *A63F 13/537* | (2014.01) |
| *A63F 13/212* | (2014.01) |

(Continued)

(52) U.S. Cl.
CPC .............. *A61B 5/375* (2021.01); *A61B 5/374* (2021.01); *A61B 5/6803* (2013.01); *A63F 13/212* (2014.09); *A63F 13/25* (2014.09); *A63F 13/28* (2014.09); *A63F 13/355* (2014.09); *A63F 13/46* (2014.09); *A63F 13/537* (2014.09); *A61B 5/168* (2013.01); *A61B 5/291* (2021.01); *A61B 5/7203* (2013.01); *A61B 5/7264* (2013.01)

(58) Field of Classification Search
CPC ........ A61B 5/0478; A61B 5/048; A61B 5/168
See application file for complete search history.

(56) References Cited

U.S. PATENT DOCUMENTS

| | | | |
|---|---|---|---|
| 6,402,520 B1 * | 6/2002 | Freer .................... | A61B 5/0482 434/236 |
| 2009/0318826 A1 * | 12/2009 | Green ................ | A61B 5/04014 600/545 |

(Continued)

*Primary Examiner* — Puya Agahi
(74) *Attorney, Agent, or Firm* — Finnegan, Henderson, Farabow, Garrett & Dunner, LLP

(57) ABSTRACT

A method and system for neuro-feedback training are disclosed. According to certain embodiments, the method may include receiving, by a processor via a communication network, a brainwave signal measured by at least one sensor attached to a user. The method may also include determining, by the processor, a frequency distribution of the brainwave signal. The method may also include determining, by the processor, a reward in a video game when at least one first value indicative of an amount of the brainwave signal within a first frequency band meets a first criterion. The method may further include providing, to the user, a first feedback signal indicative of the reward.

24 Claims, 12 Drawing Sheets

(51) Int. Cl.
*A61B 5/374* (2021.01)
*A61B 5/16* (2006.01)
*A61B 5/291* (2021.01)

(56) References Cited

U.S. PATENT DOCUMENTS

| | | | | |
|---|---|---|---|---|
| 2011/0071416 A1* | 3/2011 | Terada | ............... | A61B 5/6803 |
| | | | | 600/544 |
| 2014/0038147 A1* | 2/2014 | Morrow | ............... | A61B 5/0478 |
| | | | | 434/236 |
| 2015/0297109 A1* | 10/2015 | Garten | ............... | A61B 5/316 |
| | | | | 600/28 |
| 2015/0313496 A1* | 11/2015 | Connor | ............... | A61B 5/0478 |
| | | | | 600/301 |
| 2018/0286272 A1* | 10/2018 | McDermott et al. | .. | A61B 5/744 |

\* cited by examiner

SYSTEMS AND METHODS FOR NEURO-FEEDBACK TRAINING USING VIDEO GAMES

TECHNICAL FIELD

The present disclosure relates generally to a brain-machine interface, and more particularly, to neuro-feedback training systems and methods based on a video game and/or an Internet of Things (IoT).

BACKGROUND

Neurons, or nerve cells, in the human brain communicate through electrochemical impulses that give rise to changing electromagnetic fields, also known as brainwaves. The brainwaves can be measured outside the skull through electroencephalography (EEG). Typically, the spectrum of the brainwaves may have several distinct frequency bands, such as delta, theta, alpha, beta, and gamma bands. Studies on the brain and brain signals have shown that different brainwave frequency bands are correlated with different brain functions and various mental, emotional or cognitive states.

For example, the amplitude of the beta band increases when people pay high attention on solving certain problems, whereas the amplitude of the alpha band increases when people are less focused and more relaxed. Moreover, when people are sleeping or feel sleepy, the amplitude of their theta band increases.

As such, different neuro-feedback training methods have been developed to measure a trainee's brainwave activities and provide feedback based on the measurements to the trainee in real time, so that the trainee can become more aware of the psychophysiological processes and learn how to gain conscious control of specific brainwave frequency patterns.

However, even being enabled to view their real-time brainwave activities, most people may find it very challenging to learn how to control the frequency content of their brainwaves. In particular, the skills for controlling various mental/emotional states, such as "focus," "alertness," "relaxation," etc., are hard to grasp and cannot be easily communicated via clear verbal instructions. That is, there is no simple way to tell a trainee how to produce the desired brainwave activities as the learned behavior is non-verbal and must be experientially learned through informational feedback. Moreover, the feedback provided to a trainee is often in a simple form and lack of change (e.g., only showing a number proportional to the user's attention level or only generating an alerting sound), and is found by the trainees to be boring and not engaging.

Therefore, many neuro-feedback training methods require an experienced trainer to monitor the measured brainwave activities and guide the trainee through repeated training sessions. However, the skills for each trainer may vary so that inconsistent results may be obtained for independent trainees. However, even if trainers are used, the trainees may still be confused during the beginning of neuro-feedback training and wonder what they should do to achieve control of their brainwave activities. As a result, the trainees may become easily frustrated and lose motivation during initial training sessions. Because of at least these reasons, the typical neuro-feedback training methods are costly, time consuming, and may be perceived by the trainees as boring, repetitive, and difficult to master.

The disclosed neuro-feedback training systems and methods are directed to mitigating or overcoming one or more of the problems set forth above and/or other problems in the prior art.

SUMMARY

One aspect of the present disclosure is directed to a processor-implemented method for neuro-feedback training. The method may include receiving, by a processor via a communication network, a brainwave signal measured by at least one sensor attached to a user. The method may also include determining, by the processor, a frequency distribution of the brainwave signal. The method may also include determining, by the processor, a reward in a video game when at least a first value indicative of an amount of the brainwave signal within a first frequency band meets a first criterion. The method may further include providing, to the user, a first feedback signal indicative of the reward.

Another aspect of the present disclosure is directed to a neuro-feedback training system. The system may include at least one sensor coupled with a processor. The at least one sensor is configured to: measure a brainwave signal when the at least one sensor is attached to a user; and transmit the brainwave signal to the processor. The processor is configured to: receive the brainwave signal from the at least one sensor; determine a frequency distribution of the brainwave signal; determine a reward in a video game when at least a first value indicative of an amount of the brainwave signal within a first frequency band meets a first criterion; and provide, to the user, a feedback signal indicative of the reward.

Yet another aspect of the present disclosure is directed to a non-transitory computer-readable medium storing instructions which, when executed, cause one or more processors to perform a method for neuro-feedback training. The method may include receiving, via a communication network, a brainwave signal measured by at least one sensor attached to a user. The method may also include determining a frequency distribution of the brainwave signal. The method may also include determining a reward in a video game when at least a first value indicative of an amount of the brainwave signal within a first frequency band meets a first criterion. The method may also include providing, to the user, a feedback signal indicative of the reward.

DETAILED DESCRIPTION

This disclosure is generally directed to systems and methods for neuro-feedback training. In the disclosed embodiments, the systems collect and analyze brainwave signals of a human subject (i.e., a user of the neuro-feedback training system). Based on the user profile and the purpose of the neuro-feedback training, the systems determine which frequency band(s) of the brainwave signals should be rewarded and which frequency band(s) of the brainwave signals should be inhibited. The systems then provide feedback signals to the user in various manners, to guide and incentivize the user to reinforce the rewarded frequency band(s) and suppress the inhibited frequency band(s). In some embodiments, the system may provide the feedback signals in the form of various visual, audio, or tactile features in a video game. In some embodiments, the system may actuate a target device (e.g., a toy, a connected home appliance, or another IoT device) via a network. The resulted performance of the target device (e.g., whether the target device has successfully performed the intended actuation) provides an intuitive neuro-feedback to the user.

Figure 1:
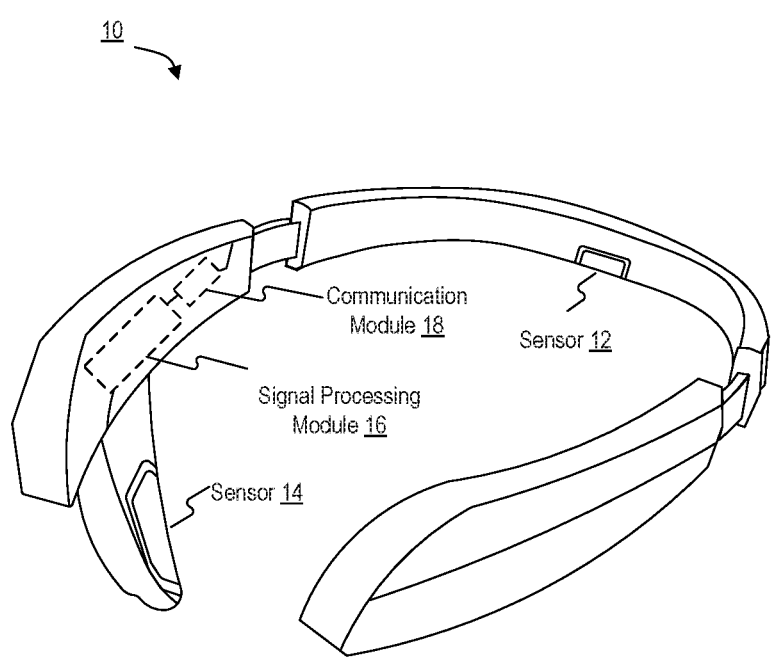
FIG. 1 is a schematic diagram illustrating a headband for measuring at least one brainwave signal, according to an exemplary embodiment.

FIG. 1 is a schematic diagram illustrating a headband 10 for measuring at least one brainwave signal, according to an exemplary embodiment. Referring to FIG. 1, headband 10 may be worn by a user. In some embodiments, headband 10 may have a U-shaped body and can wrap around a user's head. In some embodiments, headband 10 may have an adjustable length and may be made of shape memory. For example, a portion of headband 10 may be elastic or otherwise stretchable. As another example, headband 10 may have a built-in extension portion that can be hidden, extended, or partially extended to adjust the length of headband 10. As such, headband 10 can be adapted to closely fit different head dimensions.

Headband 10 may include one or more sensors for measuring brainwave signals. For example, these sensors may be medical level hydrogel sensors capable of EEG detection. The sensors may be placed at different locations of headband 10 so that they become attached to different parts of the user's head when he wears headband 10. As shown in FIG. 1, in one embodiment, sensors 12 and 14 may be mounted at different positions on the surface of headband 10, such that when headband 10 is worn by the user, sensor 12 touches the user's forehead, and sensor 14 touches one of the user's ears. The forehead is one of the commonly used scalp locations for detecting brainwave signals, while little or no brainwave signals can be recorded at the ears and their vicinities. As such, sensor 14 serves as a reference sensor, wherein the difference of the signals recorded by sensors 12 and 14 becomes the measured brainwave signal. It is contemplated sensors 12 and 14 are for illustrative purpose only. The present disclosure does not limit the number of sensors and the placements of these sensors on the scalp for recording the brainwave signals.

Headband 10 may also include an embedded signal processing module 16 for processing the signals measured by sensors 12 and 14. For example, signal processing module 16 may include one or more application specific integrated circuits (ASICs), controllers, micro-controllers (MCUs), microprocessors, or other electronic components. For example, signal processing module 16 may include an amplifier circuit that determines the difference between the signals measured by sensors 12 and 14, and amplifies the resulted brainwave signal for further analysis.

Headband 10 may also include an embedded communication module 18 configured to facilitate communication, wired or wirelessly, between headband 10 and other devices. In some embodiments, communication module 18 and signal processing module 16 may be integrated on the same circuit board. Communication module 18 can access a wireless network based on one or more communication standards, such as WiFi, LTE, 2G, 3G, 4G, 5G, etc. In one exemplary embodiment, communication module 18 may include a near field communication (NFC) module to facilitate short-range communications between headband 10 and other devices. In other embodiments, communication module 18 may be implemented based on a radio frequency identification (RFID) technology, an infrared data association (IrDA) technology, an ultra-wideband (UWB) technology, a Bluetooth (BT) technology, or other technologies. In the exemplary embodiments, signal processing module 16 may transmit, via communication module 18, the processed brainwave signals to other devices for performing the disclosed methods for neuro-feedback training.

In various embodiments, headband 10 may also include certain components not shown in FIG. 1. For example, in one embodiment, headband 10 may include one or more light-emitting diode (LED) lights for indicating the operation status of headband 10, such as on/off of headband 10, battery/power level, whether headband 10 is connected, etc. In another embodiment, headband 10 may include a micro-USB port which serves as a charging port. In another embodiment, headband 10 may include a light at the forehead position (hereinafter referred to as "forehead light"). The forehead light may indicate the current attention level as indicated by the brainwave signals detected by sensor 12, 14. For example, the forehead light may indicate the real-time attention level of the user by emitting different colors of light. For example, the red color may indicate the user is highly focused, the blue color may indicate the user is unfocused, and the green color may indicate the user is in transition between different attention levels. Additionally or alternatively, the forehead light may also indicate the user's mental state by changing the light intensities or light patterns (e.g., blinking at different frequencies). The present disclosure does not limit the method used by the forehead light to indicate the user's mental state.

Figure 2:
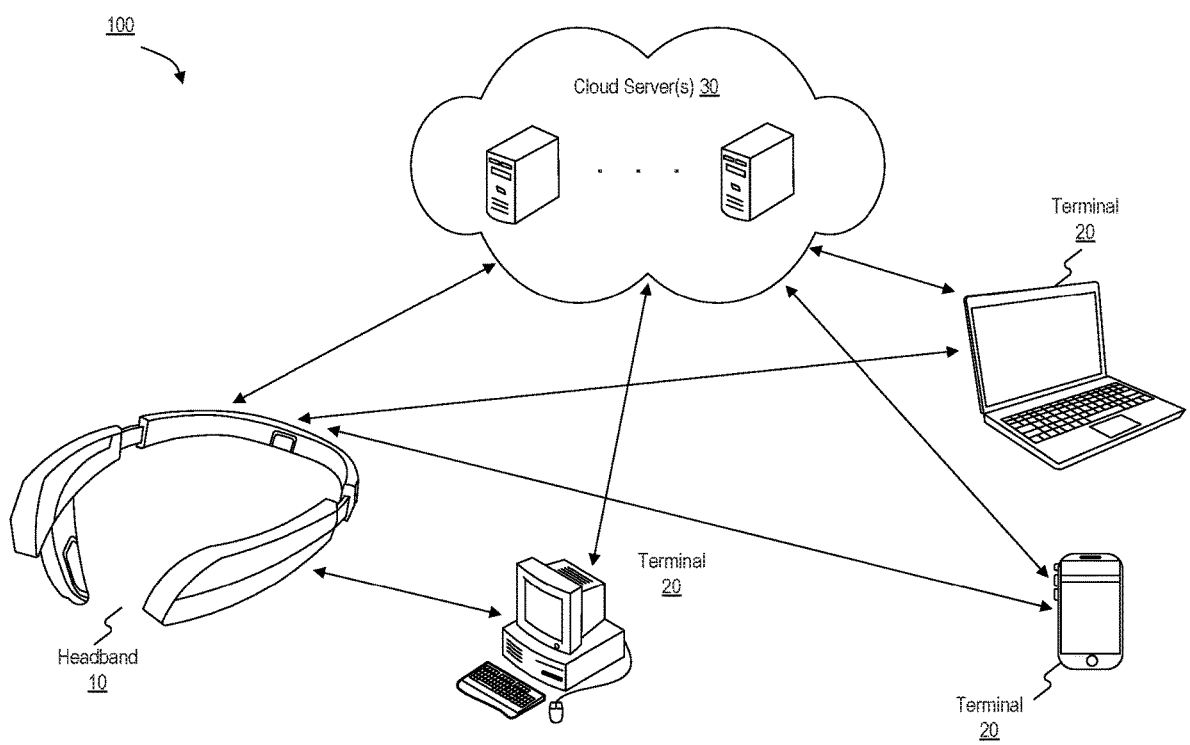
FIG. 2 is a schematic diagram illustrating a video-game based system 100 for neuro-feedback training, according to an exemplary embodiment.

In the disclosed methods for neuro-feedback training, the brainwave signals measured by headband 10 are used to generate incentives or penalties in various forms, to help the user master the control of the brain activities. For example, the incentives or penalties may be presented through a video game. FIG. 2 is a schematic diagram illustrating a video-game based system 100 for neuro-feedback training, according to an exemplary embodiment. Referring to FIG. 2, system 100 may include headband 10, one or more terminals 20, and cloud server(s) 30. Consistent with the disclosed embodiments, headband 10 may stream or otherwise transmit the measured brainwave signals to terminal 20 and/or cloud server 30 in real time. Both terminal 20 and cloud server 30 may be configured to store and/or process the measured brainwave signals.

Terminal 20 may be an electronic device with computing capabilities, such as a mobile phone, a tablet computer, a personal computer, a wearable device (e.g., a smart watch), a personal digital assistant (PDA), a remote controller, exercise equipment, an ebook reader, a MP4 (Moving Picture Experts Group Audio Layer IV) player, etc. The video games may be stored in cloud server 30, and made downloadable to terminal 20. After download, the video games may be installed on terminal 20. When the user selects a video game and starts a neuro-feedback training session, terminal 20 may load the selected video game and generate the video-game data based on the brainwave signals received from headband 10. In the disclosed embodiments, terminal 20 also includes a user interface through which the user can play the video games.

Alternatively and additionally, the video games may also be stored and run on one or more cloud servers 30. Cloud server 30 may be a general purpose computer, a mainframe computer, or any combination of these components. Cloud server 30 may be implemented as a server, a server cluster consisting of a plurality of servers, or a cloud computing service center. Cloud server 30 may be operated by a third party service provider, an administrator of the neuro-feedback training, or a manufacturer or a supplier of headband 10. In some embodiments, cloud server 30 may receive the brainwave signals from headband 10 and generate the video-game data based on the received brainwave signals. Cloud server 30 then streams the generated video-game data to terminal 20, so that the user can play the video game on terminal 20 in real time.

Figure 3:
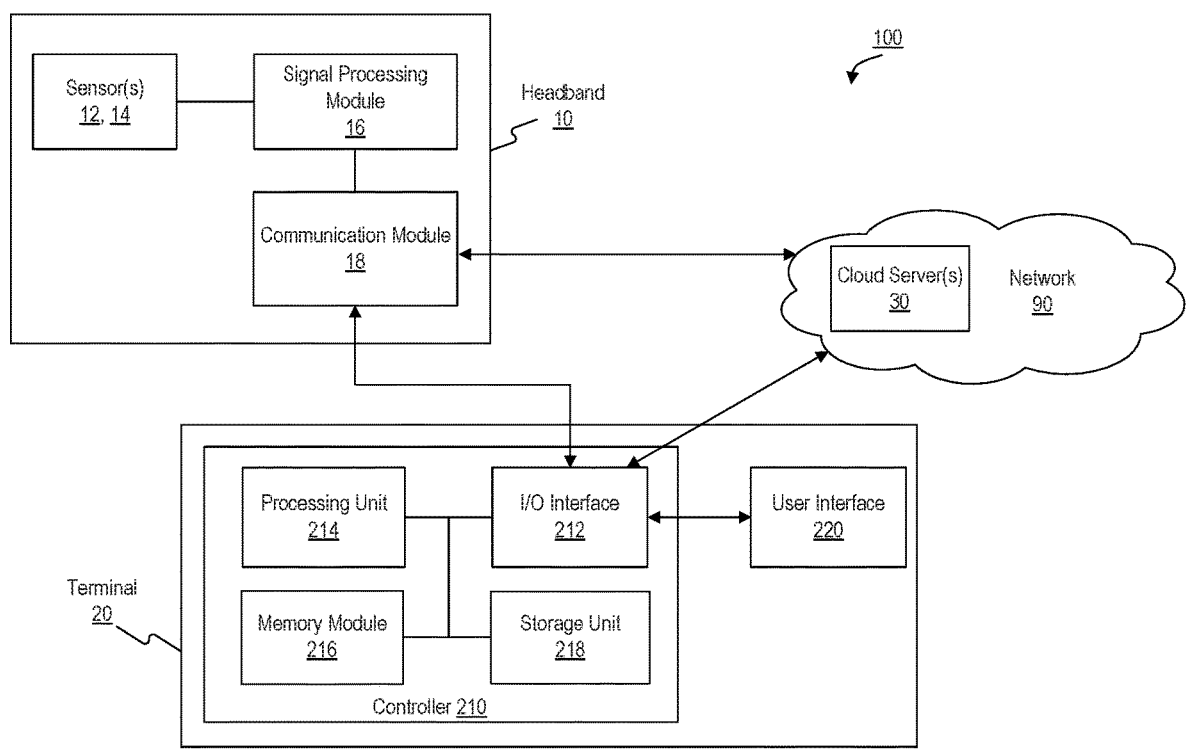
FIG. 3 is a block diagram of the system shown in FIG. 2, according to an exemplary embodiment.

FIG. 3 is a block diagram of system 100 of FIG. 2, according to an exemplary embodiment. Again, system 100 may include headband 10, one or more terminals 20, and cloud server(s) 30, connected with each other through network 90. Referring to FIG. 3, headband 10 includes but not limited to sensors 12 and 14, signal processing module 16, and communication module 18, consistent with the description in connection with FIG. 1. Headband 10 may form a wired or wireless connection with terminal 20 and/or cloud server(s) 30 via network 90. Network 90 may be any type of wired or wireless network that allows transmitting and receiving data. For example, the network may be a nationwide cellular network, a local wireless network (e.g., Bluetooth or WiFi), or a wired network.

Terminal 20 may include a controller 210 and a user interface 220. Controller 210 may include, among other things, an I/O interface 212, a processing unit 214, a memory module 216, and/or a storage unit 218. These units may be configured to transfer data and send or receive instructions between or among each other.

I/O interface 212 may be configured for two-way communication between controller 210 and various devices. For example, as depicted in FIG. 3, I/O interface 212 may send and receive signals to and from headband 10, cloud server 30, and user interface 220. I/O interface 212 may send and receive the data between each of the components via communication cables, networks (e.g., network 90), or other communication mediums.

I/O interface 212 may be configured to consolidate signals it receives from the various components and relay the data to processing unit 214. Processing unit 214 may include any appropriate type of general purpose or special-purpose microprocessor, digital signal processor, or microprocessor. Processing unit 214 may be configured as a separate processor module dedicated to performing the disclosed methods for neuro-feedback training. Alternatively, processing unit 214 may be configured as a shared processor module for performing other functions of terminal 20 unrelated to neuro-feedback training.

Processing unit 214 may be configured to receive data and/or signals from components of system 100 and process the data and/or signals to provide the neuro-feedback training. For example, processing unit 214 may receive brainwave signals from headband 10 via I/O interface 212. Processing unit 214 may further process the received brainwave signals to generated various visual and/or audio features presented in the video games. Moreover, if the video games are run on cloud server 30, processing unit 214 may also receive video-game data from cloud server 30 via I/O interface 212. In the exemplary embodiments, processing unit 214 may execute computer instructions (program codes) stored in memory module 216 and/or storage unit 218, and may perform functions in accordance with exemplary techniques described in this disclosure. More exemplary functions of processing unit 214 will be described below in relation to the disclosed methods for neuro-feedback training.

Memory module 216 and/or storage unit 218 may include any appropriate type of mass storage provided to store any type of information that processing unit 214 may need to operate. Memory module 216 and/or storage unit 218 may be a volatile or non-volatile, magnetic, semiconductor, tape, optical, removable, non-removable, or other type of storage device or tangible (i.e., non-transitory) computer-readable medium including, but not limited to, a ROM, a flash memory, a dynamic RAM, and a static RAM. Memory module 216 and/or storage unit 218 may be configured to store one or more computer programs that may be executed by processing unit 214 to perform exemplary neuro-feedback training methods disclosed in this application. For example, memory module 216 and/or storage unit 218 may be configured to store program(s) that may be executed by processing unit 214 to determine the rewards/penalties used in the video games based on the brainwave signals, and generate visual and/or audio effects showing the determined rewards/penalties.

User interface 220 may include a display panel through which the video game may be provided. The display panel may include an LCD, a liquid crystal display (LED), a plasma display, a projection, or any other type of display, and may also include microphones, speakers, and/or audio input/outputs (e.g., headphone jacks) or may be coupled to an audio system of terminal 20.

Additionally, user interface 220 may also be configured to receive input or commands from the user. For example, the display panel may be implemented as a touch screen to receive input signals from the user. The touch screen includes one or more touch sensors to sense touches, swipes, and other gestures on the touch screen. The touch sensors may not only sense a boundary of a touch or swipe action, but also sense a period of time and a pressure associated with the touch or swipe action. Alternatively or in addition, user interface 220 may include other input devices such as keyboards, buttons, joysticks, keyboards, and/or tracker balls. User interface 220 may be configured to send the user input to controller 210.

Still referring to FIG. 3, cloud server 30 may be connected to headband 10 and/or terminal 20 via network 90. Cloud server 30 may include one or more controllers (not shown), similar to the configurations of controller 210 described above.

Figure 4:
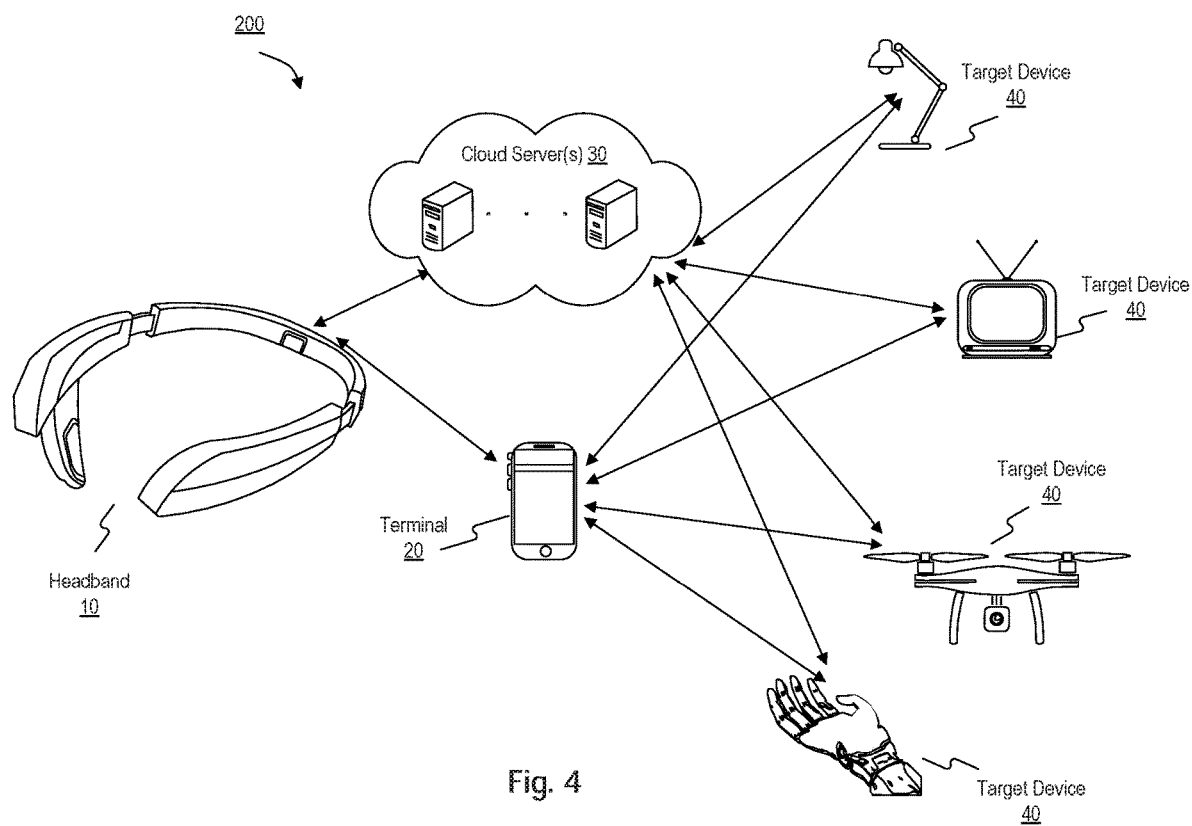
FIG. 4 is a schematic diagram illustrating an Internet-of-Things (IoT) device based system for neuro-feedback training, according to an exemplary embodiment.

In some embodiments, the neuro-feedback training may also be performed by using the measured brainwave signals to actuate a target device. The target device may be any device that connected to an IoT and thus can be remotely controlled by a controller. FIG. 4 is a schematic diagram illustrating an IoT device based system 200 for neuro-feedback training, according to an exemplary embodiment. Referring to FIG. 4, system 200 may include a headband 10, one or more terminals 20, one or more cloud servers 30, and a target device 40. Headband 10, terminal 20, and cloud server 30 may have similar structures and configurations as described above, and thus those descriptions are not repeated with respect to FIG. 3.

Target device 40 may be a device with certain computing and/or communication capabilities, such as a smart home appliance (e.g., a lamp, a television, an air condition, an air purifier, a socket, etc.), a drone, a remote-controlled vehicle, a prosthetic hand, a robot, etc. Both terminal 20 and target device 40 may connect to the same IoT, such that terminal 20 can remotely control or actuate target device 40. For example, if target device 40 is a lamp, terminal 20 may remotely turn on or off the lamp, and/or change the color of the light emitted by the lamp. As another example, if target device 40 is a TV, terminal 20 may remotely turn on or off the TV, and/or change the channel currently played by the TV. As another example, if target device 40 is a drone, terminal 20 may remotely control the rotation speed of the drone's propellers. For yet another example, if target device 40 is a prosthetic hand, terminal 20 may remotely actuate one or more fingers of the prosthetic hand to move, bend, or perform certain other actions.

In some embodiments, to perform neuro-feedback training, terminal 20 may control or actuate target device 40 based on the user's brainwaves. Specifically, after receiving the measured brainwave signals from headband 10, terminal 20 may process the brainwave signals to determine whether they meet certain predetermined conditions. When the brainwave signals meet a predetermined condition, terminal 20 may generate a corresponding control signal for actuating target device 40 and transmit the control signal to target device 40 via the IoT.

Alternatively and additionally, target device 40 may also be controlled or actuated by cloud server 30. For example, cloud server 30 may receive the brainwave signals directly from headband 10 or via terminal 20. Similar to the above description regarding terminal 20, cloud server 30 may then process the received brainwave signals and generate control signals that actuate target device 40 based on the brainwave signals.

Figure 5:
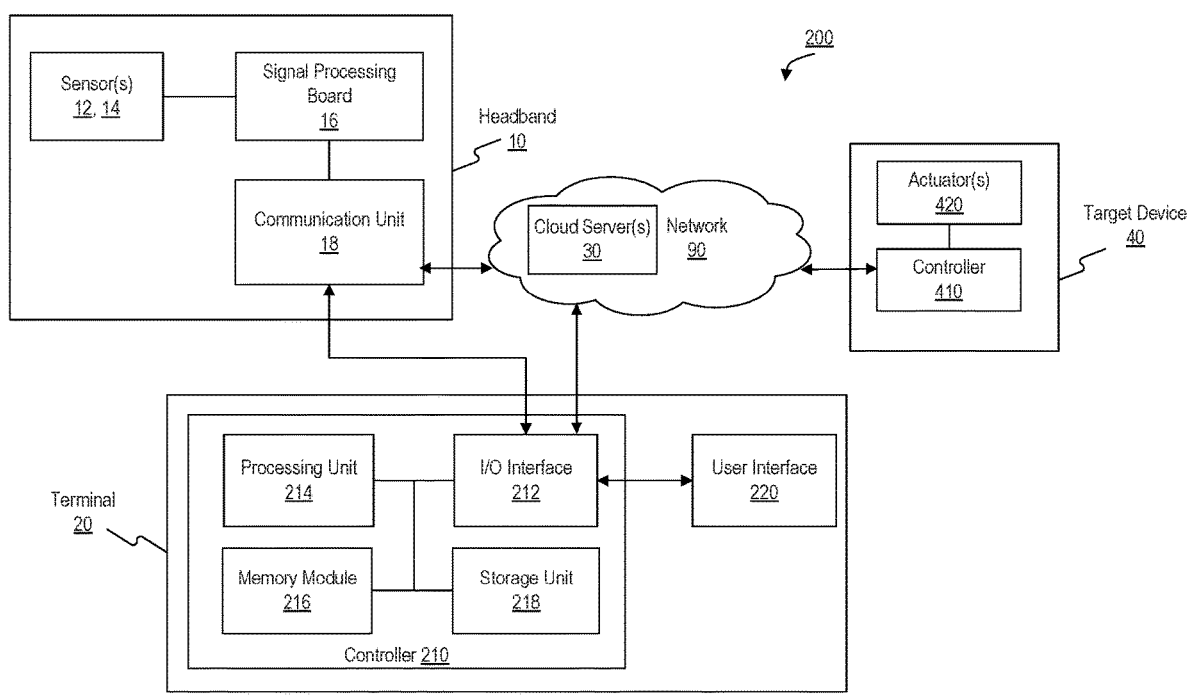
FIG. 5 is a block diagram of the system shown in FIG. 4, according to an exemplary embodiment.

FIG. 5 is a block diagram of the system 200 shown in FIG. 4, according to an exemplary embodiment. Referring to FIG. 5, headband 10, terminal 20, cloud server 30, and target device 40 may communicate with each other, wired or wirelessly, via a network, such as network 90. The structures and configurations of headband 10, terminal 20, and cloud server 30 have been described above, and thus are not repeated here. Moreover, target device 40 may include a controller 410 and one or more actuators 420. Controller 410 may receive a control signal from terminal 20 and control actuator 420 to perform a task based on the control signal. Controller 410 may adopt any suitable structure. For example, controller 410 may include one or more of the units/modules described in connection with controller 210 (FIG. 3). Actuator 420 may have various forms and structures. For example, actuator 420 may be a switch in a lamp or a TV, an electric motor in a drone or a prosthetic hand, a starter solenoid in a vehicle, etc.

Next, neuro-feedback training methods consistent with the present disclosure will be described. Without special explanation, the following description assumes the steps of the disclosed methods are performed by terminal 20. However, it is contemplated some or all of the steps in the follow described methods may also be performed by headband 10, cloud server 30, and target device 40.

According to the disclosed methods, the neuro-feedback training may be implemented by rewarding (i.e., reinforcing) one or more frequency band(s) of the brainwaves, and/or inhibiting (i.e., suppressing) one or more other frequency band(s). For example, often the lower frequency bands are associated with relaxation and day dreaming, the middle frequency bands are associated with focused thinking and problem solving, and the higher frequency bands may be indicative of anxiety, hyper vigilance, and agitation. As such, in order to improve the user's attention ability (i.e., stay focused), the mid-frequency bands, e.g., the low beta band (e.g., the band in between 13 Hz and 20 Hz) may be rewarded, while the theta band (e.g., the band in between 4 Hz and 8 Hz) and the high beta band (e.g., the band in between 22 Hz and 28 Hz) may be inhibited. Accordingly, a reward may be provided to the user when the brainwave signal has a high amplitude in the low beta band has, and a penalty may be provided when the theta band or high beta band has a high amplitude. This way, the user can be incentivized to gradually gain the abilities of reinforcing the rewarded band(s), and suppressing the inhibited band(s). Thus, the success of the neuro-feedback training depends on proper determination of the rewards and penalties (hereinafter collectively referred to as "feedback").

It is contemplated that the specific frequency bands and the frequency ranges used in this description are for illustrative purpose only. The present disclosure does not limit which frequency bands and/or frequency ranges are to be rewarded and/or inhibited.

Figure 6:
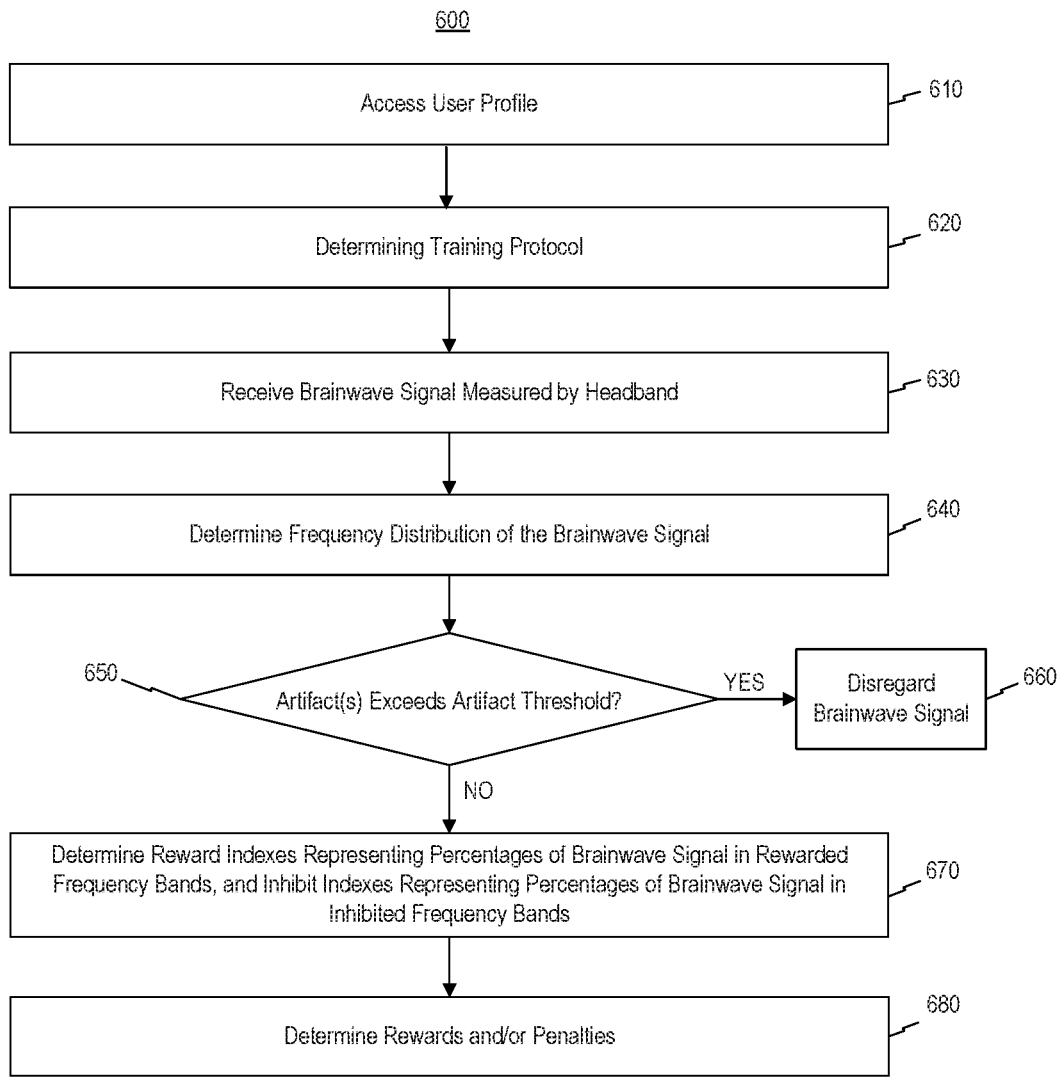
FIG. 6 is a flowchart of a method for determining a feedback based on a brainwave signal, according to an exemplary embodiment.

FIG. 6 is a flowchart of a method 600 for determining a feedback based on a brainwave signal, according to an exemplary embodiment. For example, terminal 20 may be installed with an application for neuro-feedback training. To start a neuro-feedback session, the user may put on headband 10 and activate headband 10 to record the brainwave signal. Meanwhile, the user may then initiate the application, such that terminal 20 may establish a wireless connection with headband 10 and perform method 600. Referring to FIG. 6, method 600 may include the following steps 610-670.

In step 610, terminal 20 accesses the user profile before the neuro-feedback training. For example, different people may have different EEG characteristics. That is, terminal 20 may require the user to input the user's age, gender, and other demographic information. For example, statistics show that the alpha peak range for people in different age groups may be different. In one embodiment, terminal 20 may set the alpha peak range for users under or at 10 years old to be [8.5 Hz, 9.5 Hz], and set the alpha peak range for users above 10 years old to be [9.5 Hz, 10.5 Hz]. This way, terminal 20 can select the proper frequency bands to be rewarded and/or inhibited.

In step 620, terminal 20 determines a training protocol for the current neuro-feedback training session. Depending on the goal of the neuro-feedback training, terminal 20 may determine the rewarded frequency band(s) and the inhibited frequency band(s). For example, improving attention and focus may require rewarding the low beta band and inhibiting the theta and high beta bands; assisting with meditation or improving relaxation may require rewarding the alpha and theta bands; improving mental fitness may require inhibiting all the frequency bands, etc. As such, terminal 20 may prompt the user to select a goal for the neuro-feedback training. Based on the selection, terminal 20 may determine the proper rewarded and/or inhibited frequency bands.

In step 630, terminal 20 receives one or more brainwave signals measured by headband 10. The brainwave signals may be measured continuously over time, or during set time intervals. Terminal 20 may then apply a low-pass filter to remove the signal noise and derive the power spectrum of the brainwave signal, e.g., using mathematic methods such as a Fourier transform (step 640). As described above, the amplitudes of the power spectrum may be grouped into different frequency bands. Besides the normal bands showing the brain activities, sometimes the power spectrum may also include one or more frequency bands corresponding to artifacts. For example, eye blinking, biting, and other facial muscle movements may give rise to one or more distinct artifact bands. When the amplitude of the artifact is high than certain level, the whole power spectrum may be distorted and render inaccurate feedback determination. Thus, in step 650, terminal 20 may determine whether the power spectrum encompasses one or more predetermined artifact bands. If the artifact bands are present, terminal 20 may further determine whether the amplitude of the artifact bands exceeds their respective artifact threshold. If at least one artifact band has an amplitude higher the respective artifact threshold, terminal 20 may disregard the brainwave signal received during the period of time in which the artifact is detected (step 660). Otherwise, terminal 20 may conclude the brainwave signal is valid and proceeds to step 670.

In step 670, terminal 20 determines one or more reward indexes indicative of the percentages of the brainwave signal in the rewarded frequency bands, and one or more inhibit indexes indicative of percentages of the brainwave signal in the inhibited frequency bands. Specifically, terminal 20 may divide the amplitudes of the rewarded and inhibited frequency bands by the overall amplitude of the full power spectrum, to determine the respective reward and inhibit indexes.

In step 680, terminal 120 determines the rewards and/or penalties based on the determined reward and inhibit indexes. Specifically, terminal 20 may compare the reward and inhibit indexes to the respective reward and inhibit thresholds. Initial values may be assigned to the reward and inhibit thresholds at the beginning of the neuro-feedback training. In some embodiments, the reward threshold may take a value in the range of 0.5-0.9 (or alternatively 50%-90%). For example, the reward threshold may be set around 0.8 (or 80%). The inhibit threshold may take a value in the range of 0.05-0.3 (or 5%-30%), e.g., 0.2 (or 20%). The thresholds may be adjusted throughout the training based on the user's performance Generally, the user is expected to control the brainwave activities so as to keep the reward indexes above the respective reward thresholds and keep the inhibit indexes below the respective inhibit thresholds. As such, the reward and inhibit thresholds set the goal of the neuro-feedback training. If at least one inhibit index exceeds the corresponding inhibit threshold, terminal 20 may conclude that a penalty shall be assessed. In contrast, if no inhibit index exceeds the inhibit thresholds and at least one reward index exceeds the corresponding reward threshold, terminal 20 may conclude that a reward shall be assessed.

In some embodiments, the reward may have multiple levels corresponding to multiple reward thresholds. Specifically, terminal 20 may determine the reward level by comparing a reward index to the multiple reward thresholds. For example, three reward thresholds, 0.6. 0.7, and 0.8, may be set by terminal 20, corresponding to a low reward level, a medium reward level, and a high reward level. Accordingly, reward index falling in between 0.6 and 0.7 is assigned the low reward level, while a reward index exceeding 0.8 is assigned the high reward level.

Figure 7:
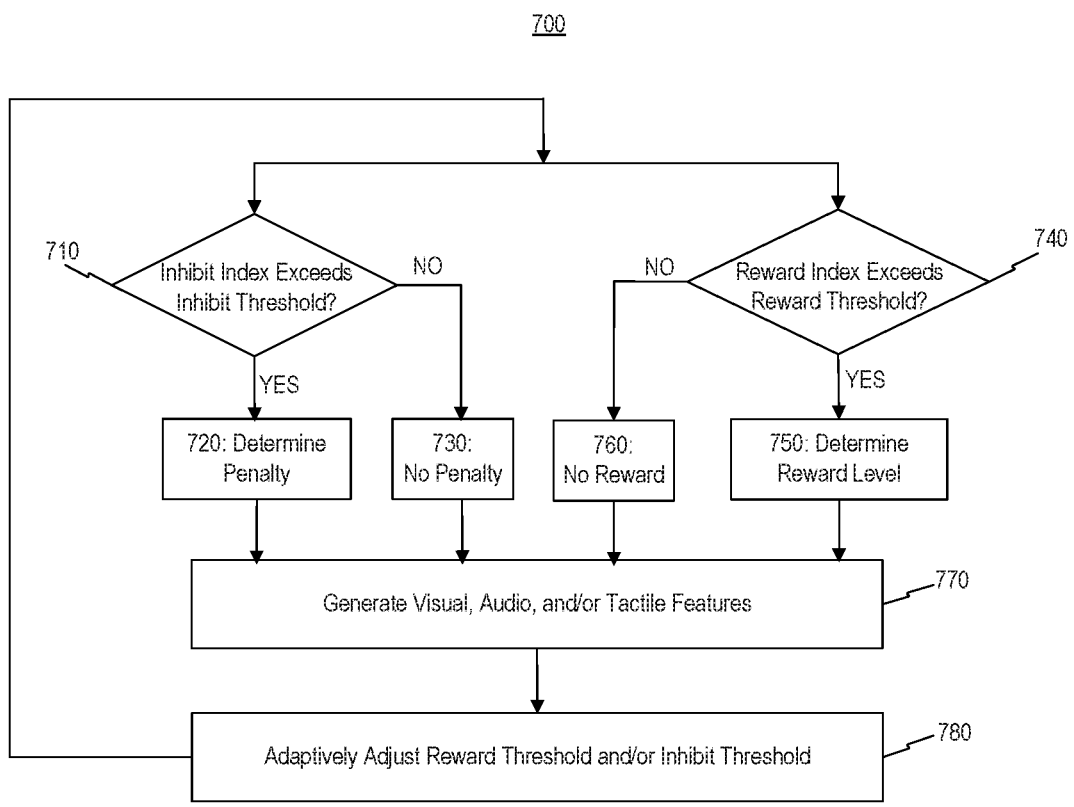
FIG. 7 is a flowchart of a method for neuro-feedback training based on a video game, according to an exemplary embodiment.

FIG. 7 is a flowchart of a method 700 for neuro-feedback training based on a video game, according to an exemplary embodiment. For example, method 700 may be performed by system 100. Referring to FIG. 7, method 700 may include the following steps 710-760.

In step 710, terminal 20 may determine whether an inhibit index exceeds the corresponding inhibit threshold. When the inhibit index exceeds the corresponding inhibit threshold, terminal 20 may conclude that a penalty should be generated in the video game and further determine the penalty (step 720). Otherwise, terminal 20 may conclude that no penalty should be generated (step 730).

Terminal 20 may also determine whether a reward index exceeds the corresponding reward threshold (step 740). When the reward index exceeds the corresponding reward threshold, terminal 20 may conclude that a reward should be generated in the video game, and further determine the reward level if multiple reward levels are defined in the video game (step 750). Otherwise, terminal 20 may conclude that no reward should be generated (step 760). Here, the processes for determining the penalty and/or reward (or reward levels) may be similar to steps 670-680.

Figure 8:
FIG. 8 is a schematic diagram illustrating a scene of a video game for neuro-feedback training, according to an exemplary embodiment.

In step 770, terminal 20 may generate various visual, audio, and/or tactile features based on the results determined in steps 720, 730, 750, and 760. FIG. 8 is a schematic diagram illustrating a scene 800 of a video game for neuro-feedback training, according to an exemplary embodiment. As shown in FIG. 8, the video game may feature a main character 810, which can be controlled by the user to navigate around an oasis 820. Oasis 820 may include multiple scenes, each of which may correspond to a training session and may last for a predetermined amount of time, e.g., 20-30 minutes. In each scene, main character 810 may encounter various characters 830 and animals 840. Each scene may have a particular script that requires main character 810 to complete certain tasks. Characters 830 may interact with main character 810 and guide main character 810 to finish the tasks.

Figure 9A:
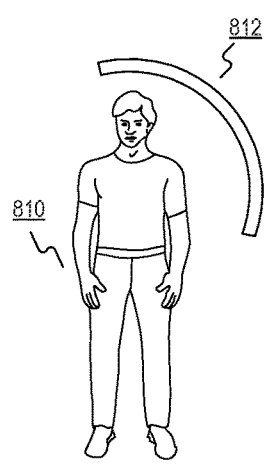
FIGS. 9A-9C are schematic diagrams illustrating a visual feature indicative of rewards achieved in the video game shown in FIG. 8, according to an exemplary embodiment.
Figure 9B:
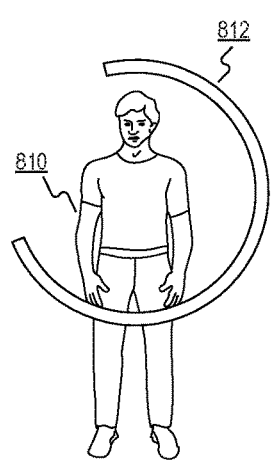
Figure 9C:
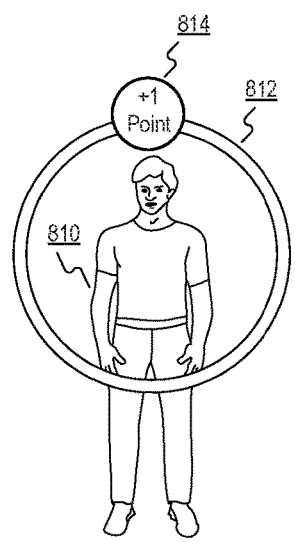

The video game may provide visual and/or audio features based on the determined rewards and penalties. FIGS. 9A-9C are schematic diagrams illustrating certain exemplary visual features indicative of rewards achieved in the video game shown in FIG. 8. Referring to FIGS. 9A-9C, the video game may display a status ring indicating the progress of main character 810 in achieving the rewards. Specifically, the status ring fills at a speed proportional to the reward index. For example, in one embodiment, the video game may use four reward levels, represented by the integers "1," "2," "3," and "4." If the reward level is at 1, the status bar may fill up every 4 minutes. If the reward level is at 2, the status bar may fill up every 3 minutes. If the reward level is at 3, the status bar may fill up every 2 minutes. If the reward level is at 4, the status bar may fill up every 1 minute. Moreover, if there is no reward, the status bar will stay unchanged.

In some embodiments, a score may be given to main character 810 to record the user's progress in doing the neuro-feedback training. Referring to FIG. 9C, when a status ring is filled up, terminal 20 may display a message 814 indicating the user has gained one more point. Meanwhile, terminal 20 may also generate a prompting sound, such as a beeping sound, to indicate to the user that a point has been gained. As such, the faster the status ring fills, the faster the user's score increases. This creates an incentive for the user to progress through the neuro-feedback training. Although FIGS. 9A-9C show a status ring associated with providing rewards, it is contemplated that other visual features, such as status bar (filling up horizontally or vertically), a water tank, a color changing palette, spinning reels as in a slot machine, etc. For example, the status bar or the water tank may fill up to reward attentions, and the speed it fills up may be proportional to the reward index or reward level. As another example, the reels may stop spinning and let the user gamble for a virtual jackpot when he is paying attention.

Figure 10:
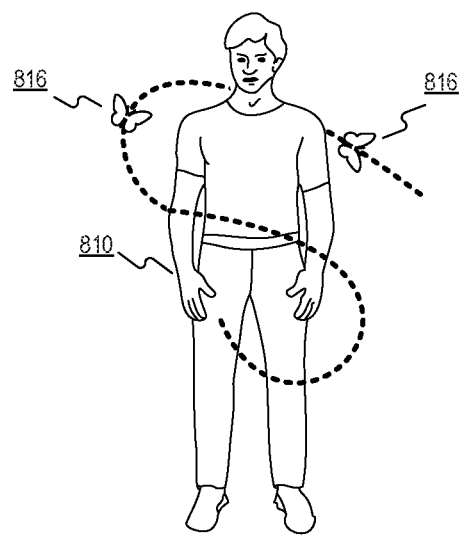
FIG. 10 is a schematic diagram illustrating a visual feature indicative of penalties achieved in the video game shown in FIG. 8, according to an exemplary embodiment.

In some embodiments, the video game may also use certain visual features to indicate the penalties. FIG. 10 is a schematic diagram illustrating a visual feature indicative of penalties achieved in the video game shown in FIG. 8, according to an exemplary embodiment. For example, as shown in FIG. 10, the video game may include two fireflies 816 following main character 810. The two fireflies 816 may correspond to two different inhibit indexes (i.e., two inhibited frequency bands) separately. When the inhibit indexes are low (i.e., no penalty), fireflies 816 may be displayed as normal, flying around main character 810. However, as an inhibit index increases, the corresponding firefly 816 gradually fades. When the inhibit index exceeds the corresponding inhibit threshold, i.e., reaching a penalty, the corresponding firefly 816 completely disappears. In some embodiments, the video game may also use certain audio features to indicate the penalties. For example, terminal 20 may generate a prompting sound when a penalty is reached. As another example, terminal 20 may emit a warning sound continuously while an inhibit index stay above the corresponding inhibit threshold.

In some embodiments, terminal 20 may also generate tactile signals for indicating the rewards and/or penalties. For example, terminal 20 may be a mobile phone that can generate various types of vibrations. The vibrations may alert the user that a reward and/or a penalty has been achieved.

Figure 11:
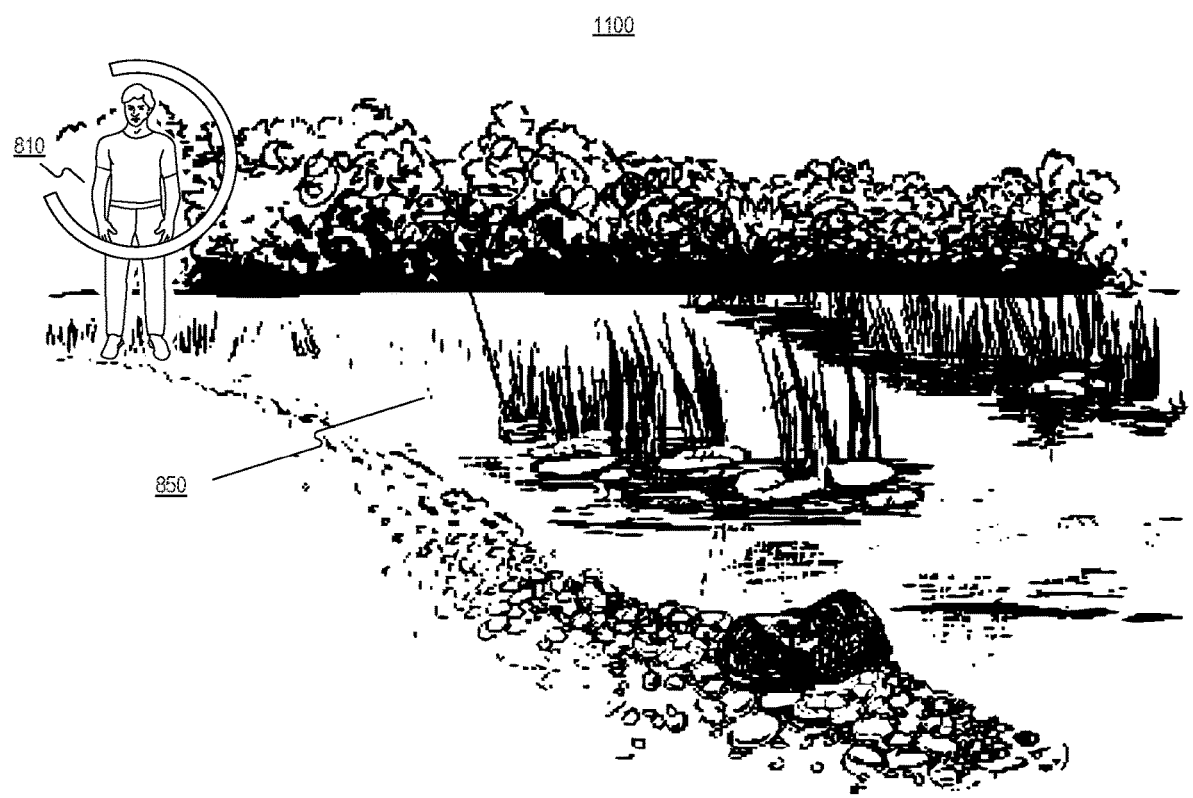
FIG. 11 is a schematic diagram illustrating a scene of a video game used for neuro-feedback training, according to an exemplary embodiment.

Consistent with the disclosed embodiments, the video game may contain various other mechanisms to generate the visual, audio, and/or tactile features. FIG. 11 is a schematic diagram illustrating a scene 1100 of a video game used for neuro-feedback training, according to an exemplary embodiment. As depicted in FIG. 11, main character 810 is standing by a pond 850. In some embodiments, scene 1100 may become more enjoyable, e.g., brighter, more colorful, having more aesthetic features, etc., whenever the user achieves a reward. For example, pond 850 may be initially empty. As the user progresses to accumulate the rewards, pond 850 may be filled with more and more water lilies and fishes. As such, scene 1100 may become more enjoyable at a pace proportional to the user's progress in achieving the rewards.

Referring back to FIG. 7, in step 780, terminal 20 adaptively adjusts the reward thresholds and/or inhibit thresholds based on the user's progress in achieving the rewards and/or penalties. For example, at the initial stage of the neuro-feedback training, the user may be unskilled in controlling the brainwave activities. If the user constantly receives a penalty and fails to achieve any reward, the user may easily accumulate frustration and quickly lose interest in playing the video game. Thus, terminal 20 may set the reward thresholds low and the inhibit thresholds high, so that it is easier for the user to achieve the reward and avoid the penalty. After the user engages the training for certain amount of time, the user may be able to achieve the rewards in a faster speed and can better avoid the penalties. As such, terminal 20 may gradually increase the reward thresholds and lower the inhibit thresholds, so as to gradually increase the difficulty level of the neuro-feedback training. As another example, terminal 20 may continuously monitor the pace of the user in completing the tasks in each scene and/or the speed in accumulating the required scores for each scene. When terminal 20 finds that the time spent by the user in a particular scene is longer than a predetermined amount of time (e.g., 30 minutes), terminal 20 may lower the reward thresholds and increase the inhibit thresholds, so as to prevent user frustration. In some embodiments, machine learning methods, such as regression algorithms or Bayesian algorithms, may be employed to study the user's historical performance in the video game and find the proper reward and inhibit thresholds that lead to an optimal incentive level for motivating the user to keep engaging the neuro-feedback training.

As described above, neuro-feedback training may also be provided by using the brainwave signal to control a target device connected to an IoT. In particular, the user's success or failure in actuating the target device provides intuitive guidance and incentive for the user to perform the neuro-feedback training. As such, the target device may serve as a "toy" or an educational tool for assisting the user in learning the skills of controlling the brainwave activities.

Figure 12:
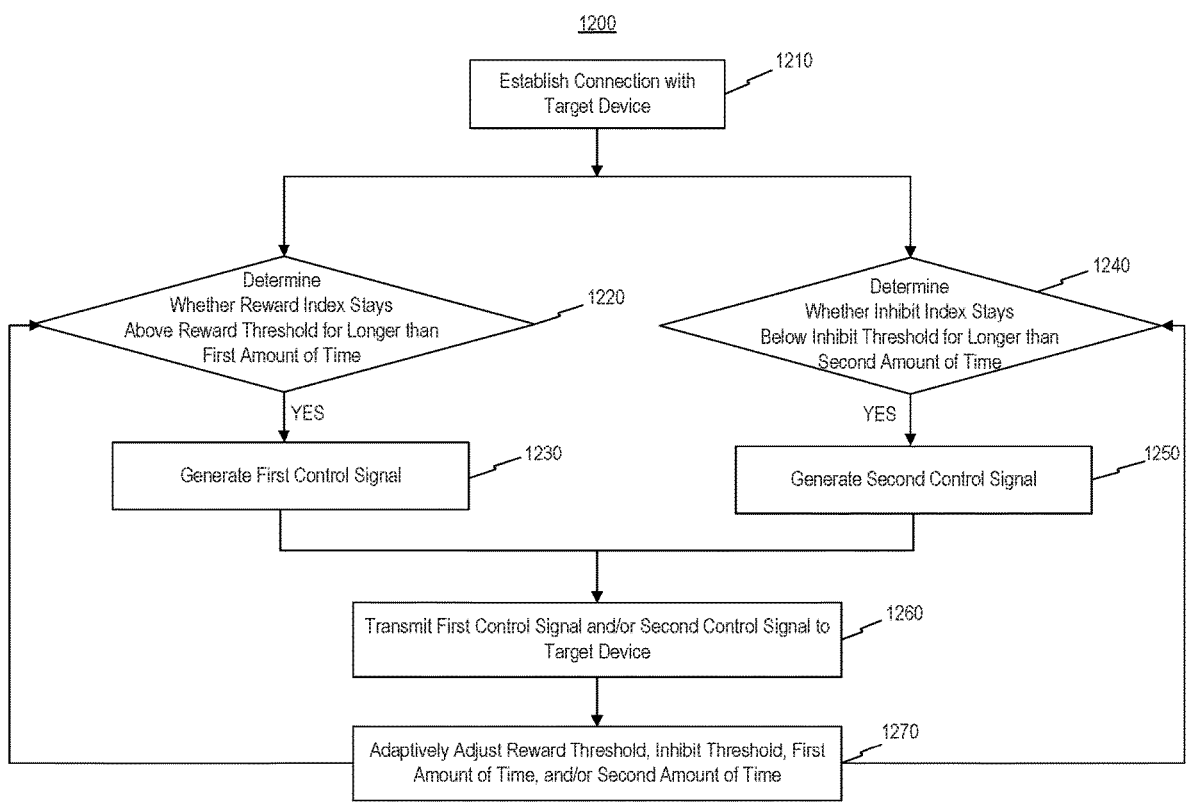
FIG. 12 is a flowchart of a method for neuro-feedback training based on an IoT device, according to an exemplary embodiment.

FIG. 12 is a flowchart of method 1200 for neuro-feedback training based on an IoT device, according to an exemplary embodiment. For example, method 1200 may be performed by system 200. Referring to FIG. 12, method 1200 may include the following steps 1210-1270.

In step 1210, terminal 20 establishes connection with target device 40. In some embodiments, headband 10 and/or terminal 20 can only form a wireless connection, e.g., WiFi or Bluetooth™ connection, with a device located within a certain distance of terminal 20 or the user. As such, the user may first bring the distance between terminal 20 and target device 40 within the workable rage of WiFi or Bluetooth™ signals. Further, in order to provide feedback, target device 40 should be within a visible range from the user. The user may then operate terminal 20 to initialize an application for neuro-feedback training, after which terminal 20 may automatically scan for available IoT devices around terminal 20. If terminal 20 finds target device 40, headband 10 and/or terminal 20 may automatically pairs with target device 40. In some embodiments, terminal 20 may discover multiple devices surrounding terminal 20. In this case, the user may manually select target device 40 from among the discovered devices. Alternatively, terminal 20 may include a distance sensor configured to measure the distances between terminal 20 and the surrounding devices, and automatically choose the device with the closest proximity to terminal 20 or the user as target device 40. In some embodiments, the distance sensor may be a GPS sensor.

After the connection is established, terminal 20 may determine whether a reward index stays above the corresponding reward threshold for longer than a first amount of time (step 1220). If yes, terminal 20 may generate a first control signal to actuate target device 40 (step 1230).

In some embodiments, terminal 20 is capable of controlling or actuating multiple target devices 40. As such, the actuation may be preprogramed for target device 40. In one embodiment, each target device 40 may be assigned a unique identifier, such as a media access control address (MAC address). By reading the unique identifier, terminal 20 may determine the identity of currently connected target device 40 and the type of actuation preprogramed for target device 40. For example, when target device 40 is a lamp, the first control signal may be configured to instruct the lamp to turn on or off. Alternatively, the lamp may be turned on once the reward index exceeds the reward threshold, and the brightness of the lamp may be continuous dimmed as the index stays above the threshold. In another embodiment, when target device 40 is a drone, the first control signal may be configured to instruct the drone to take off from the ground. Alternatively, the drone may be program to take off once the reward index exceeds the reward threshold, and continue to be propelled as the index stays above the threshold.

In some embodiments, terminal 20 may actuate target device 40 differently based on the value of the reward index. In one embodiment, terminal 20 may control a lamp to change its light color based on the values of the reward index. For example, when the reward index is in between 0.6 and 0.7, the color may be set to be white; when the reward index is in between 0.7 and 0.8, the color may be changed to red; and when the reward index is above 0.8, the color may be changed to green. With the color change, the user can immediately know the current level of reward index and be motivated to work hard to increase the reward index.

In some embodiments, terminal 20 may also actuate target device 40 differently based on the period of time during which the reward index continuously stays above the reward threshold. In one embodiment, terminal 20 may rotate the propellers of a drone at a speed proportional to the time duration in which the user maintains the reward index above the reward threshold. That is, as the reward index stays above the reward threshold longer, the propellers rotate faster and finally the drone can take off. In another embodiment, the number of fingers of a prosthetic hand actuated by terminal 20 may be proportional to the time duration in which the reward index continuously stays above the reward threshold. For example, in the first 5 seconds, terminal 20 may only drive the index finger to move. In the next 5 seconds, terminal 20 may drive the middle finger to move. Such control schemes make the neuro-feedback training a rewarding and fun experience, and thus make it easier for the user to master the ability of maintaining a particular frequency pattern of the brainwaves.

Still referring to FIG. 12, alternatively or additionally, terminal 20 may also actuate target device 40 based on the inhibit indexes. That is, terminal 20 may determine whether an inhibit index stays below the corresponding inhibit threshold for longer than a second amount of time (step 1240). If yes, terminal 20 may generate a second control signal to actuate target device 40 (step 1250). The detailed implementation of steps 1240 and 1250 are similar to the above description in connection with steps 1220 and 1230, which is not repeated here.

In step 1260, terminal 20 transmits the first control signal and/or the second control signal to target device 40, such that target device 40 may perform the desired actuations based on the first control signal and/or the second control signal.

In step 1270, terminal 20 adaptively adjusts the training parameters such as the reward threshold, the inhibit threshold, the reward frequency band, the inhibit frequency band, the first amount of time, and the second amount of time based on the user's performance in actuating target device 40. Similar to step 760 (FIG. 7), here terminal 20 may adjust the thresholds and amounts of time to fine tune the incentive level and/or difficulty level of the neuro-feedback training. In some embodiment, machine learning algorithms may be employed by terminal 20 to determine the proper values for the thresholds and amounts of time, so as to optimize the difficulty level of neuro-feedback training for each individual user. For example, as the user trains with target device 40, terminal 20 may gradually increase the reward threshold and/or lower the inhibit thresholds, so as to increase the difficulty level of controlling target device 40. As another example, when terminal 20 finds the user repeatedly fails to actuate target device 40, terminal 20 may shorten the first amount of time and/or the second amount of time. By making it easier to control target device 40, the user may be encouraged and motivated to stay with the training. This way, the effectiveness of the neuro-feedback training can be improved. Similar to the descriptions above with respect to step 760, as part of step 1270, the frequency bands may also be adaptively or dynamically adjusted during the neuro-feedback training based on the user's performance and brainwave characteristics learned during the process.

In the above description of method 1200, although the first/second control signal and thus the neuro-feedback are generated based on the comparing of the reward/penalty index (i.e., percentages of the brainwave signal in the rewarded/inhibited frequency bands) to the reward/penalty threshold, terminal 20 may also use other information extracted from the brainwave signals to actuate target device 40. For example, in some embodiments, terminal 20 may actuate target device 40 based on the presence, absence, and/or amplitudes of certain designated bands in the detected brainwave signals. Specifically, when terminal 20 determines that a designated band has an amplitude higher than a predetermined amplitude level, terminal 20 may generate a corresponding control signal for actuating target device 40. For example, such designated band may correspond to eye blink, such that the user may control target device 40 by blinking one or both eyes.

In general, although methods 600, 700, and 1200 are described in connection with the frequency features of the brainwave signals, the present disclosure is not limited to the frequency features. Rather, it is intended that the disclosed methods and systems may use any suitable features of the brainwave signals. For example, one phenomena known as Event Related Potential (ERP) refers to a significant change in a brainwave signal following specific stimulus (e.g., viewing certain scenes or hearing a specific music). For example, a user's exposure to certain stimuli may create a significant change in the brainwave signal's amplitude approximately 300 milliseconds after the exposure (also known as "P300 ERP"). Such change may be used to detect the user's response to a stimuli and generate neuro-feedbacks.

In exemplary embodiments, the data used and generated by the disclosed methods for neuro-feedback training may be saved in, for example, memory module 216 and/or storage unit 218 for further study and analysis. In one embodiment, the data may be analyzed to optimize the neuro-feedback training for each individual user. For example, memory module 216 and/or storage unit 218 may store a user profile assisted with each user. The user profile may include but are not limited to each user's age, gender demographic information, EEG characteristics, and past brainwave signals generated during the neuro-feedback training. Machine learning methods, such as regression algorithms or Bayesian algorithms, may be employed to analyze the user profile and optimize (or customize) the neuro-feedback training for the individual user. For example, when the analysis of a particular user's past training data shows that the user responds to a first reward threshold better than a second reward threshold, the first reward threshold may be used more frequently for this user. As another example, when the analysis shows that a specific type of feedback (e.g., a particular type of feedback feature used in a video game or actuating a particular target device 40) works best for the user, such type of feedback may be used more frequently for the user.

In another embodiment, the past training data for multiple users may be aggregated for big-data analysis. For example, the brainwave signals associated with multiple users and data indicating these users' performance in their neuro-feedback training may be aggregated. Various data-mining methods may be employed to study the aggregated data and discern patterns, trends, and any other types of statistics shown by the multiple users. The findings may be used to optimize the algorithm used in the disclosed methods for neuro-feedback training methods, and/or used for research purposes, such as brain medial research.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage unit or the memory module having the computer instructions stored thereon, as disclosed. In some embodiments, the computer-readable medium may be a disc or a flash drive having the computer instructions stored thereon.

It is contemplated the disclosed methods for neuro-feedback training may have various applications, both medical and non-medical. For example, as mentioned above, the disclosed methods may be used for training and improving attention related behaviors. As such, the disclosed methods may be used for effectively relieving or treating attention related medical conditions, such as ADHD (attention deficit hyperactivity disorder). The present disclosure does not limit the application areas of the disclosed methods and systems.

It will be apparent to those skilled in the art that various modifications and variations can be made to the disclosed neuro-feedback training systems and related methods. Other embodiments will be apparent to those skilled in the art from consideration of the specification and practice of the disclosed neuro-feedback training system and related methods. It is intended that the specification and examples be considered as exemplary only, with a true scope being indicated by the following claims and their equivalents.

What is claimed is:

1. A neuro-feedback training method performed by a video game application executed by a mobile terminal, the method comprising:
   repeatedly generating a plurality of types of feedback signals during a current neuro-feedback training session, the plurality of types of feedback signals comprising at least a visual cue, an audio cue, and a tactile cue;
   executing a machine learning algorithm to analyze data showing a user's performance during one or more past neuro-feedback training sessions, wherein the executing of the machine learning algorithm selects a first type of feedback signals from the plurality of types of feedback signals, the selecting being based at least partially on the user's neuro-feedback training performance in response to the plurality of types of feedback signals, respectively;
   generating, in the computer game, the first type of feedback signals at an increased frequency;
   receiving a brainwave signal, via a communication network, the brainwave signal being measured by at least one sensor attached to the user;
   determining a frequency distribution of the brainwave signal, wherein the frequency distribution comprises a first frequency band and a second frequency band;
   determining a reward in the video game application, in response to:
      a first value indicative of an amount of the brainwave signal within the first frequency band stays above an initial value of a first threshold for a first time period, and
      a second value indicative of an amount of the brainwave signal within the second frequency band is below a second threshold during the first time period;
   providing, to the user, a first feedback signal indicative of the reward, wherein the first feedback signal is one of the first type of feedback signals, and providing the first feedback signal comprises displaying, on the mobile terminal, a first animation corresponding to the first value and a second animation corresponding to the second value; and
   adaptively adjusting the first threshold or the first time period, based on a determination of whether the first value stays above the initial value of the first threshold for the first time period.

2. The method of claim 1, wherein the first value is a percentage of the brainwave signal within the first frequency band.

3. The method of claim 1, wherein displaying the first animation comprises:
   displaying a status bar which fills at a speed proportional to a progress of the user in achieving the reward.

4. The method of claim 1, wherein:
   the reward has a plurality of reward levels; and
   displaying the first animation comprises:
      determining a reward level corresponding to the first value; and
      generating the first feedback signal based on the determined reward level.

5. The method of claim 4, wherein:
   the user is associated with a score in the computer game; and
   the method further comprises:
      increasing the score at a speed proportional to the determined reward level.

6. The method of claim 5, wherein displaying the first animation comprises:
   displaying a status bar representing a progress of the user in achieving the reward; and
   when the score increases, filling up the status bar.

7. The method of claim 5, further comprising:
   when the score increases, generating a prompting sound indicating the score has changed.

8. The method of claim 1, further comprising:
   when at least one second value meets a criterion, determining a penalty in the computer game; and
   providing, to the user, a second feedback signal indicative of the penalty, the second feedback signal being one of the first type of feedback signals.

9. The method of claim 8, wherein providing the second feedback signal indicative of the penalty comprising:

removing the second animation from the video game application.

10. The method of claim 8, further comprising:
adaptively adjusting the criterion based on a progress of the user in achieving the penalty.

11. The method of claim 1, further comprising:
assessing the user before the neuro-feedback training; and
determining the first and second frequency bands based on the assessment.

12. The method of claim 11, wherein assessing the user includes at least one of:
determining an age of the user; or
accessing characteristics of the brainwave signals of the user.

13. The method of claim 1, wherein the mobile terminal is wirelessly connected with the at least one sensor.

14. The method of claim 1, wherein the at least one sensor is mounted on a headband worn by the user.

15. The method of claim 1, wherein the method is used to train attention related behaviors.

16. The method of claim 15, wherein the method is used to treat attention deficit hyperactivity disorder (ADHD).

17. A neuro-feedback training system, comprising:
at least one sensor coupled with a mobile terminal, the at least one sensor being configured to:
  measure a brainwave signal when the at least one sensor is attached to a user; and
  transmit the brainwave signal to the mobile terminal;
wherein the mobile terminal is configured to execute a video game application installed on the mobile terminal, the video game application being configured to:
  repeatedly generate a plurality of types of feedback signals during a current neuro-feedback training session, the plurality of types of feedback signals comprising at least a visual cue, an audio cue, and a tactile cue;
  execute a machine learning algorithm to analyze data showing a user's performance during one or more past neuro-feedback training sessions, wherein the executing of the machine learning algorithm selects a first type of feedback signals from the plurality of types of feedback signals, the selecting being based at least partially on the user's neuro-feedback training performance in response to the plurality of types of feedback signals, respectively;
  generate, in the computer game, the first type of feedback signals at an increased frequency;
  receive the brainwave signal from the at least one sensor;
  determine a frequency distribution of the brainwave signal, wherein the frequency distribution comprise a first frequency band and a second frequency band;
  determine a reward in the video game application, in response to:
    a first value indicative of an amount of the brainwave signal within the first frequency band stays above an initial value of a first threshold for a first time period, and
    a second value indicative of an amount of the brainwave signal within the second frequency band is below a second threshold during the first time period;
  provide, to the user, a feedback signal indicative of the reward, wherein the first feedback signal is one of the first type of feedback signals, and providing the first feedback signal comprises displaying, on the mobile terminal, a first animation corresponding to the first value and a second animation corresponding to the second value; and
  adaptively adjust the first threshold or the first time period, based on a determination of whether the first value stays above the initial value of the first threshold for the first time period.

18. The system of claim 17, wherein the mobile terminal is further configured to:
when at least one second value meets a criterion, determine a penalty in the computer game; and
provide, to the user, a second feedback signal indicative of the penalty, the second feedback signal being one of the first type of feedback signals.

19. The system of claim 17, wherein the mobile terminal is wirelessly connected with the at least one sensor.

20. The system of claim 17, wherein the system is used to treat attention deficit hyperactivity disorder (ADHD).

21. A non-transitory computer-readable medium storing instructions of a video game application which, when executed by a mobile terminal, cause the mobile terminal to perform a method for neuro-feedback training, the method comprising:
repeatedly generating a plurality of types of feedback signals during a current neuro-feedback training session, the plurality of types of feedback signals comprising at least a visual cue, an audio cue, and a tactile cue;
executing a machine learning algorithm to analyze data showing a user's performance during one or more past neuro-feedback training sessions, wherein the executing of the machine learning algorithm selects a first type of feedback signals from the plurality of types of feedback signals, the selecting being based at least partially on the user's neuro-feedback training performance in response to the plurality of types of feedback signals, respectively;
generating, in the computer game, the first type of feedback signals at an increased frequency;
receiving a brainwave signal via a communication network, the brainwave signal being measured by at least one sensor attached to the user;
determining a frequency distribution of the brainwave signal, wherein the frequency distribution comprise a first frequency band and a second frequency band;
determining a reward in the video game application, in response to:
  a first value indicative of an amount of the brainwave signal within the first frequency band stays above an initial value of a first threshold for a first time period, and
  a second value indicative of an amount of the brainwave signal within the second frequency band is below a second threshold during the first time period; and
providing, to the user, a feedback signal indicative of the reward, wherein the first feedback signal is one of the first type of feedback signals, and providing the first feedback signal comprises displaying, on the mobile terminal, a first animation corresponding to the first value and a second animation corresponding to the second value; and
adaptively adjusting the first threshold or the first time period, based on a determination of whether the first value stays above the initial value of the first threshold for the first time period.

22. The method of claim 1, further comprising:
filtering the received brainwave signal to generate a power spectrum of the brainwave signal, wherein the power spectrum includes the plurality of frequency bands.

23. The system of claim 17, wherein the mobile terminal is further configured to:
filter the received brainwave signal to generate a power spectrum of the brainwave signal, wherein the power spectrum includes the plurality of frequency bands.

24. The method of claim 1, further comprising:
before the reward is determined, detecting whether the plurality of frequency bands include a predetermined artifact band;
in response to the plurality of frequency bands including the predetermined artifact band, determining whether the predetermined artifact band has an amplitude exceeding a first threshold; and
in response to the predetermined artifact band having an amplitude exceeding the first threshold, disregarding the predetermined artifact band.

\* \* \* \* \*